(12) United States Patent
Neumann et al.

(10) Patent No.: US 7,215,878 B2
(45) Date of Patent: May 8, 2007

(54) CHIP THAT COMPRISES AN ACTIVE AGENT AND AN INTEGRATED HEATING ELEMENT

(75) Inventors: Hermann Neumann, Haan (DE); Dietmar Kalder, Langenfeld (DE); Heinrich W. Steinel, Wörishofen (DE)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/181,087

(22) PCT Filed: Jan. 3, 2001

(86) PCT No.: PCT/EP01/00013

§ 371 (c)(1),
(2), (4) Date: Jul. 12, 2002

(87) PCT Pub. No.: WO01/50849

PCT Pub. Date: Jul. 19, 2001

(65) Prior Publication Data

US 2003/0049025 A1    Mar. 13, 2003

(30) Foreign Application Priority Data

Jan. 13, 2000    (DE) ................. 100 01 035

(51) Int. Cl.
*F24F 6/00*    (2006.01)

(52) U.S. Cl. ...................... 392/390; 392/395

(58) Field of Classification Search ............... 392/386, 392/390, 392, 394, 395; 239/34, 44, 53, 239/54, 55, 56, 60
See application file for complete search history.

(56) References Cited

U.S. PATENT DOCUMENTS

| 2,692,327 | A | * | 10/1954 | Avrigan, Jr. ............... 392/390 |
| 3,274,372 | A | * | 9/1966 | Rudolph .................... 392/387 |
| 4,037,352 | A | | 7/1977 | Hennart et al. ............. 43/129 |
| 4,037,353 | A | * | 7/1977 | Hennart et al. ............. 43/129 |
| 4,251,714 | A | * | 2/1981 | Zobele ...................... 392/392 |
| 4,663,315 | A | | 5/1987 | Hasegawa et al. ........... 514/86 |
| 4,837,421 | A | * | 6/1989 | Luthy ........................ 392/390 |
| 5,213,523 | A | * | 5/1993 | Hygema et al. ............ 439/620 |
| 6,154,607 | A | * | 11/2000 | Flashinski et al. ......... 392/390 |
| 6,296,865 | B1 | | 10/2001 | Dujardin et al. ........... 424/409 |
| 2001/0055604 | A1 | | 12/2001 | Kalder et al. .............. 424/405 |

FOREIGN PATENT DOCUMENTS

| DE | 19605581 | 8/1997 |
| DE | 19731156 | 1/1999 |
| FR | 2292430 | 6/1976 |
| FR | 2322546 | 1/1977 |
| GB | 2153227 | 8/1985 |

* cited by examiner

Primary Examiner—Sang Y. Paik

(57) ABSTRACT

Active compound chip and process for the production of an active compound chip comprising an active compound which is bound at room temperature, at least one heating element being located at least partly in the interior of the chip and the heating element having an electrical resistance and at least two electrical contacts.

24 Claims, 7 Drawing Sheets

CHIP THAT COMPRISES AN ACTIVE AGENT AND AN INTEGRATED HEATING ELEMENT

CROSS-REFERENCE TO RELATED APPLICATIONS

This application is a national stage application of PCT/EP01/00013 which was filed on Jan. 3, 2001, which in turn claims priority based on German patent application 10001035.0 filed Jan. 13, 2000.

STATEMENT REGARDING FEDERALLY SPONSORED RESEARCH/DEVELOPMENT

Not applicable

BACKGROUND OF THE INVENTION

The invention relates to an active compound chip having an integrated heating element for evaporating active compounds from the active compound chip. The invention furthermore relates to a process for the production of an active compound chip having an integrated heating element.

Various devices for the evaporation of active compounds such as insecticides or fragrances are known.

A device suitable for this purpose is a plate evaporater, consisting of a heating apparatus and insecticide plates. The insecticide plates consist of materials such as cellulose or cotton board, asbestos or ceramic and are impregnated with pyrethroid insecticides. The insecticide plates are placed on the heating apparatus, which can typically generate a temperature in range from 120 to 190° C. The insecticides are evaporated from the plates by the heat of the heating apparatus. The duration of action with plate evaporators is restricted to approximately 12 hours because of the high working temperature and the uneven release of active compound.

A similar principle underlies the gel evaporator (DE 197 31 156 A1 ), in which insecticides are incorporated into a gel formulation.

Another possibility for the evaporation of active compounds consists in the use of "liquid evaporators", in which a liquid formulation of the active compound is continuously evaporated by warming by means of a wick system (GB 2 153 227).

Polymeric active compound carriers, into which insecticidal active compounds are incorporated, are known from DE 196 05 581 A1. These polymeric active compound carriers theoretically have a working temperature of 60 to 150° C. In practice, however, it has been shown that a continuous rate of release of the active compound over a period of time of up to 60 days in a biologically active amount can only be realized using a large surface which is impracticable for the application or using a temperature in the range from 140 to 150° C. For the evaporation of the active compound, the polymeric active compound carriers are placed on a heating apparatus, such as is already known for plate and gel evaporators. Tests have shown that in the range from 110 to 100° C. the release rate of the active compound and thus the biological activity greatly decreases.

All known evaporator systems need an external heating apparatus in order to generate the heat necessary for the evaporation of the active compound. Such a heating apparatus causes additional expense and needs a certain space at the site of application. Moreover, it leaves room for faulty operation. If, for example, a controllable heating apparatus is concerned, a wrong temperature adjustment can lead to over- or underdosage of the active compound. If a controllable heating apparatus is not concerned, different heating apparatuses must be bought for the evaporation of active compounds having different evaporation temperatures.

A disadvantage of the known evaporator systems is furthermore the low efficiency caused by the heating apparatus. The heat transfer between the heating apparatus and the active compound carrier is poor, since complete contact between the surfaces of active compound carrier and heating plate is not achieved and an insulating layer of air can form between parts of the active compound carrier and the heating apparatus. This leads to the fact that it takes a long time until the active compound carrier is warmed so strongly that the active compound evaporates. High temperatures of the heating apparatus are needed in order to evaporate the active compound in an amount which is necessary, for example, for the effective control of insects. These high temperatures also border on the housing, so that there is a danger of burning for the user. At high temperatures, there is also the danger that other parts of the active compound formulation than the active compound itself evaporate and contribute to unnecessary pollution of the environment.

The poor heat transfer furthermore leads to incomplete liberation of the active compound from the active compound carrier. In the case of polymeric active compound carriers which had been heated on a heating plate, a residue of up to 20% of active compound was measured in the active compound carrier.

On account of the poor heat conductivity of the polymers and possibly occurring deformations of the active compound carriers, exact temperature control is not possible, so that uneven escape of active compound can occur.

The known systems have the further disadvantage that the non-heated surfaces of the heating apparatus, in particular, are in some cases so cool that the released active compound immediately condenses on them again.

BRIEF SUMMARY OF THE INVENTION

It was an object of the invention to find a device for the evaporation of active compounds which manages without an external heating apparatus and thereby does not have the disadvantages associated with an external heating apparatus.

The solution to the object according to the invention consists in an active compound chip comprising an active compound which is bound at room temperature, at least one heating element being located at least partly in the interior of the chip and the heating element having an electrical resistance and electrical contacts. The heating element can be heated and the active compound can be evaporated by applying an electrical voltage to the electrical contacts.

The temperature in the specified heating element is controlled via the applied voltage U in combination with the resistance R of the heating element. Since the total heating power P of the heating element is converted into the warming of the active compound chip, an exact control of the escape of active compound is possible. The amount of the escaping active compound increases with the temperature of the heating element. The local distribution of the escape of active compound depends on the heat conductivity of the active compound chip and the geometry of heating element and chip.

The heating element can consist of a conductive material which can be processed mechanically, such as ceramic, heat conductor (heating wire), vapor-deposited film or conductive plastic.

The heating element can also consist of a heating resistance or a resistance known, for example, from the publication of Siemens Matushita Components GmbH u. Co KG (Order No. from Siemens: B 425-P2562 or on the Internet under www.siemens.com\pr\index.htm, pp. 19 to 40) having a positive temperature coefficient (PTC or alternatively called cold conductor). A PTC consists, for example, of a mixture of barium carbonate, titanium oxide and further materials.

The electrical resistance of the heating element is preferably between 10 k$\Omega$ and 100 k$\Omega$ at 230V supply voltage and between 2 k$\Omega$ and 30 k$\Omega$ at 110V supply voltage. The electrical resistance R=$\rho$×l/A is determined on the one hand by the selection of the material for the heating element (specific resistance P) or the amount of electrically conductive material in the parent material, such as ceramic or plastic, on the other hand by the material thickness A and the length l of the heating element. The heating power P of the heating element is preferably between 0.1 W and 5 W and is dependent on the operating voltage U according to P=$U^2$/R. Using a heating power of 0.1 W to 5 W, temperatures in the range from 60° C. to 140° C. can preferably be established.

The heating element can assume any desired forms, which are selected depending on the desired heat distribution and surface of the heating element.

In one embodiment, the heating element has the form of a meander having at least one bend, the two electrical contacts being located on the two ends of the meander.

Preferably, the heating element has the form of two meanders having at least one bend, one electrical contact in each case being located on each end of the two meanders and it being possible for the electrical contacts facing one another of the two meanders to be connected to one another in an electrically conducting manner. This embodiment has the particular advantage that either both meanders can be contacted separately or together. The possibility thus exists to keep the heating power P=$U_1^2$/$R_1$+$U_2^2$/$R_2$ constant even at different voltages.

The meander form of the heating element guarantees a uniform heat distribution in the chip.

In other embodiments, the heating element has the structure of a lattice or of honeycombs. Lattices or honeycombs likewise guarantee an even heat distribution in the chip. In a specific embodiment, the heating element having the lattice or honeycomb structure can be designed in two strips which in each case contacts at one end and are connected to one another in an electrically conducting manner at the end opposite to the contacting.

The electrical contacts preferably consist of sheet brass or of copper.

The geometric shape of the active compound chip having an integrated heating element depends on the field of application and on the manufacturing process.

In the simplest case, the active compound chip forms a rectangular plate having electrical contacts in extension of the plate on one of the sides. If the active compound chip contains, for example, an active compound for controlling cockroaches, it can be necessary to apply the active compound chip at the base behind bars, so that it lies flats and as close as possible to the wall or bottom. In this case, the electrical connections are can be arranged perpendicular to the surface of the plate.

The active compound chip having an integrated heating element in the form of a rectangular plate preferably has a length in the range from 10 to 100 mm, a breadth in the range from 5 to 100 mm and a thickness in the range from 3 to 20 mm.

A number of heating elements can also be integrated into an active compound chip such that various areas of the active compound chip, which in each case are allocated to one heating element, can be heated in succession.

In another embodiment, the heating element is not embedded in a flat chip, but the heating element is surrounded, according to its length, by the chip part comprising the active compound so that the shape of the heating element forms an image on the external shape of the active compound chip.

The heating element can be attached directly to a current supply by means of suitably shaped electrical contacts. It can, however, also be attached to a current supply by means of a suitable adapter consisting of a holder and the power connection. One and the same adapter can be employed for active compound chips having different active compounds and thus different evaporation temperatures. It can have still further objects such as, for example, the picking up of voltage variations or the provision of additional functions.

The active compound can be present pure or as an active compound mixture in liquid, gelatinous or in solid form. In this case, the active compound chip is provided with a surface layer which is impenetrable to the active compound or the active compound mixture in liquid, gelatinous or solid form and penetrable in gaseous form. As soon as the active compound or the active compound mixture becomes gaseous as a result of the temperature increase due to the heating apparatus, it can penetrate the surface layer.

The liquid or gelatinous or solid active compound or the active compound mixture is present in a housing and the heating element is embedded in it.

Alternatively, the active compound can also be bound to an active compound carrier, preferably this active compound carrier is a polymer. Particularly preferably, the active compound chip in this case consists essentially of the heating element and the active compound carrier containing active compound surrounding this.

The active compound carrier of one preferred embodiment consists of mixtures which contain at least one active compound and least one polymer having a crystallite melting range between 100 and 300° C., preferably between 150 and 250° C., particularly preferably between 150 and 200° C. The softening range is confirmed in the case of amorphous thermoplastic polymers by the glass temperature and in the case of partially crystalline polymers by the melting temperature. Moreover, organic or inorganic auxiliaries such as stabilizers or dyes can be incorporated into the mixtures as further additives.

Active compounds which can be used in all embodiments of the active compound carriers are insecticidal active compounds such as pyrethroids, acaricidal active compounds, fragrances or ethereal oils. Preferably, transfluthrin is used as active compound. Transfluthrin displays an insecticidal action against mosquitoes, flies and cockroaches.

The pyrethroid active compounds preferably used are:
1) natural pyrethrum,
2) 3-allyl-2-methyl-cyclopent-2-en-4-on-1-yl d/l-cis/trans-chrysanthemate (allethrin/Pynamin®),
3) 3-allyl-2-methyl-cyclopent-2-en-4-on-1-yl d-cis/trans-chrysanthemate (Pynamin forte®),
4) d-3-allyl-2-methyl-cyclopent-2-en-4-on-1-yl d-trans-chrysanthemate (Exrin®),
5) 3-allyl-2-methyl-cyclopent-2-en-4-on-1-yl d-trans-chrysanthemate (Bioallethrino®),
6) N-(3,4,5,6-tetrahydrophthalimido)-methyl dl-cis/trans-chrysanthemate (phthalthrin, Neopynamin®), 7) 5-benzyl-3-furylmethyl d-cis/trans-chrysanthemate (resmethrin, Chryson forte®),
8) 5-(2-propargyl)-3-furylmethyl chrysanthemate (Furamethrin®),
9) 3-phenoxybenzyl-2,2-dimethyl-3-(2,2-dichlorovinyl) cyclopropane carboxylate (permethrin, Exmin®),
10) phenoxybenzyl d-cis/trans-chrysanthemate (phenothrin, Sumithrin®),
11) -cyanophenoxybenzylisopropyl-4-chlorophenyl acetate (fenvalerate, Sumicidin®),
12) (S)- -cyano-3-phenoxybenzyl-(1R,cis)-3-(2,2-dichlorovinyl)-2,2-dimethyl cyclopropanecarboxylate,
13) (R,S)- -cyano-3-phenoxybenzyl-(1R,1S)-cis/trans-3-(2, 2-dichlorovinyl)-2,2-dimethyl cyclopopanecarboxylate,
14) -cyano-3-phenoxybenzyl d-cis/trans-chrysanthemate,
15) 1-ethinyl-2-methyl-2-pentenyl cis/trans-chrysanthemate,
16) 1-ethinyl-2-methyl-2-pentenyl-2,2-dimethyl-3-(2-methyl-1-propenyl) cyclopropane-1-carboxylate,
17) 1-ethinyl-2-methyl-2-pentenyl-2,2,3,3-tetramethyl cyclopropanecarboxylate,
18) 1-ethinyl-2-methyl-2-pentenyl-2,2-dimethyl-3-(2,2-dichlorovinyl) cyclopropane-1-carboxylate,
19) 2,3,5,6-tetrafluorobenzyl-(+)-1R-trans-2,2-dimethyl-3-(2,2-dichlorovinyl) cyclopropanecarboxylate (transfluthrin, Bayothrin®)

or mixtures of these active compounds.

Particularly preferably, the active compounds used are 3-allyl-2-methyl-cyclopent-2en-4-on-1-yl d-cis/trans-chrysanthemate (Pynamin forte®) and 2,3,5,6-tetrafluorobenzyl-(+)-1R-trans-2,2-dimethyl-3-(2,2-dichlorovinyl) cyclopropanecarboxylate (transfluthrin).

The acaricidal active compound preferably used is benzyl benzoate.

Suitable fragrances are natural fragrances such as, for example, musk, civet, amber, casterum and similar fragrances: ajowa oil, almond oil, amber seeds absol., angelica root oil, aniseed oil, basil oil, laurel oil, benzoin resinoid, bergamot essence, birch oil, rosewood oil, broom absol., cajeput oil, cananga oil, gapiscum oil, caraway oil, cardamon oil, carrot seed oil oil, cassia oil, cedarwood oil, celery seed oil, cinnamon bark oil, citronella oil, oil of clary sage, oil of cloves, oil of cognac, coriander oil, cubeb oil, camphor oil, dill oil, tarragon oil. Eucalyptus oil, fennel oil, sweet, calbanum resinoid, garlic oil. Geranium oil, ginger oil, grapefruit oil, hop oil, hyacinth absol., jasmine absol., oil of juniper berries, labdanum resinoid, lavender oil, oil of laurel leaves, lemon oil, lemongrass oil, oil of lovage, oil of mace, mandarin oil, misoma absol., myrrh absol., mustard oil, narcissus absol., neroli oil, nutmeg oil, oak moss absol., olibanum resinoid, onion oil, opoponax resinoid, orange oil, orange blossom oil, iris concete, pepper oil, peppermint oil, peru balsam, petit grain oil, pine needle oil, rose absol., rose oil, rosemary oil, sandalwood oil, sage oil, spearmint oil, styrax oil, oil of thyme, tolu balsam, tonka beans absol., tuberose absol., turpentine oil, vanilla beans absol., vetiver oil, violet leaves absol., ylang-ylang oil and similar plant oils etc.

Also suitable are synthetic fragrances such as pinene, limonene and similar hydrocarbons; 3,3,5-trimethylcyclohexanol, linalool, geraniol, nerol, citronellol, menthol, borneol, borneylmethoxycyclohexanol, benzyl alcohol, anisyl alcohol, cinnamyl alcohol, β-phenylethyl alcohol, cis-3-hexanol, terpineol and similar alcohols; anetholes, musk xylene, isoeugenol, methyleugenol and similar phenols; amylcinnamaldehyde, anisaldehyde, n-butyraldehyde, cuminaldehyde, cyclamenaldehyde, decylaldehyde, isobutyraldehyde, hexylaldehyde, heptylaldehyde, n-nonylaldehyde, nonadienol, citral, citronellal, hydroxycitronellal, benzaldehyde, methyl-nonylacetaldehyde nonylacetaldehyde, cinnamaldehyde, dodecanol, -hexylcinnamaldehyde, undecanal, heliotropin, vanillin, ethylvanillin and similar aldehydes, methyl amyl ketone, methyl β-naphthyl ketone, methyl nonyl ketone, musk ketone, diacetyl, acetylpropionyl, acetylbutyryl, carvone, methone, camphor, acetophenone, p-methylacetophenone, ionone, methylionone and similar lactones; amylbutyrolactone, diphenyl oxide, methyl phenylglycidate, nonylacetone, coumarin, cineol, ethylmethylphenyl glycidate and similar lactones or oxides, methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl caproate, butyl heptylate, octyl caprylate, methyl heptinecarboxylate, methyl octinecarboxylate, isoamyl caprylate, methyl laurate, ethyl myristate, methyl myristate, ethyl benzoate, methylcarbinylphenyl acetate, isobutylphenyl acetate, methyl cinnamate, styracin, methyl salicylate, ethyl anisate, methyl anthranilate, ethyl pyruvate, ethyl- -butyl butyrate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl valerate, isobornyl acetate, linalyl acetate, methyl anthranilate, methyl dihydrojasmoate, nonyl acetate, βphenylethyl acetate, trichloromethylene phenyl-carbinylacetate, terpinyl acetate, vetiveryl acetate and similar esters. These fragrances can be used individually, or at least two thereof can be used as a mixture with one another. Besides the fragrance, the formulation according to the invention can optionally additionally contain the additives which are customary in the fragrance industry, such as patchouli oil or similar volatility-inhibiting agents, such as eugenol or similar viscosity-regulating agents.

Polymeric materials used for the active compound carrier are preferably amorphous and partially crystalline polymers and mixtures of the two, which can be processed under thermoplastic conditions, i.e. as viscous melts, and whose softening range lies below the boiling point of the active compounds to be incorporated under normal pressure. The polymers are chosen for the appropriate active compound such that the active compound mixes at least partially with the polymers.

Suitable amorphous polymers preferably used are:

PVC (SOFT), polystyrene, styrene/butadiene, styrene/acrylonitrile, acrylonitrile/butadiene/styrene, polymethyl acrylate, amorphous polycycloolefins, cellulose esters, aromatic polycarbonates, amorphous aromatic polyamides, poly-phenylene ethers, poly(ether) sulphones, polyimides.

Suitably partially crystalline polymers which are preferably used are:

polyethylene, polypropylene, polybutylene, PVC (HARD), polyamide, polyether amides, polyester amides, polyoxymethylene, poly-4-methylpent-1-ene, polyethylene terephthalate, polybutylene terephthalate, polyimide, polyether (ether) ketone and polyurethanes.

Preferred mixtures are, for example: blends of polycarbonates with polybutylene terephthalate, blends of polyamide-6 and styrene/acrylonitrile.

Polypropylene, amorphous aromatic polyamides, aromatic polycarbonates and aromatic polyurethanes and ®TPX types, ®Desmopan 8410, ®Vestamid 1800, ®BAK 402-005 are particularly preferred.

The mixtures can be stabilized with the aid of antioxidants by admixing a UV absorber to the formulation as an additive. UV absorbers which can be employed are all known UV absorbers.

Those preferably employed are phenol derivatives, such as, for example, butylhydroxytoluene (BHT), butylhydroxyanisole (BHA), bisphenol derivatives, aryl-amines, such as, for example, phenylnaphthylamine, phenyl-β-naphthylamine, a condensate of phenetidine and acetone or the like or benzophenones.

It is possible to use dyes, such as inorganic pigments, e.g. iron oxide, titanium oxide, ferric ferrocyanide and inorganic dyes, such as, for example, alizarin, azo and metal phthalocyanine dyes and metal salts, such as salts of iron, manganese, boron, copper, cobalt, molybdenum and zinc.

By means of the active compound concentration and amount, the duration of action can be adjusted in a period of time of 1 to 60 10-hour nights.

The active compound chips in general contain between 0.1 and 80% by weight, preferably between 0.2 and 40% by weight, particularly preferably between 1.0 and 20% by weight, of active compound.

Additional functions can be integrated either into the chip or into the adapter.

The active compound chip can additionally be equipped with an operating display. This can consist of an LED, preferably a bipolar LED, and can be connected in series, for example, with the heating element.

Between the current supply and the contacts of the active compound chip, it is possible to employ a timer chip known per se. In addition to the contacts present, a resistance is then integrated into the active compound chip or into the adapter. This resistance should preferably be arranged asymmetrically, such that the active compound chip is contacted to the current supply or the timer chip only in one of two possible positions of incorporation. The incorporated resistance is controlled by the timer function set on the timer chip such that after the end of a preselected time the current contact terminates. The user has the possibility by simple rotation of the chip to choose between two types of operation (with timer/without timer). Alternatively, the choice between two different timer periods would also be conceivable.

For the stabilization of the temperature in the case of variations of the ambient temperature, a resistance having a positive temperature coefficient can be incorporated into the apparatus. If the ambient temperature and thus the temperature in the chip falls, the temperature on the PTC thus decreases. As a result of the decrease in the temperature in the PTC, the resistance of the PTC also decreases and the PTC heats to compensate.

For the production of an active compound chip in which the active compound or the active compound mixture is present in liquid, gelatinous or solid form, a heating element is sprayed onto an endless metal tape. The individual heating elements are subsequently punched out of the endless metal tape, the contacts are separated and the heating elements are enclosed in a housing. The active compound or the active compound mixture is added to the heating element in the housing, provided the housing does not yet contain the active compound or the active compound mixture, and the housing is sealed.

Similarly, an active compound chip having a heating element consisting of two strips can be produced. Each strip is sprayed onto two endless metal tapes. One endless metal tape is cut between each two strips, the other endless metal tape between each strip. The heating elements produced in this manner are enclosed in a housing which contains the active compound carrier. For the integration of an operating display, the first metal tape can also be cut between each strip. An LED is then soldered in between each two strips.

For the production of an active compound chip in which the active compound is bound to an active compound carrier, a heating element is sprayed onto at least one endless metal tape. The active compound carrier containing the active compound is subsequently sprayed around the heating element on the endless metal tape and the individual active compound chips are then punched out of the tape of active compound carriers on the endless metal tape.

For the production of an active compound chip in which the active compound is bound to an active compound carrier and the active compound carrier is a polymer and the heating element is a conductive plastic, the heating element together with the active compound carrier can be extruded, in the form that, for example, a plastic wire is produced whose core forms the heating element and whose jacket forms the active compound carrier. This plastic wire can assume any desired shape, for example a meander shape.

In a further embodiment, a heating element made of strips having a lattice or honeycomb structure is sprayed onto at least one endless metal tape. The individual heating elements are subsequently punched out of the endless metal tape and the contacts are optionally separated and the active compound or the active compound mixture is introduced into the honeycomb or lattice structure of the heating element using a doctor blade, namely in liquid, waxy or thermoplastic form. For the introduction using the doctor blade, the active compound or the active compound mixture is distributed into the interstices of the lattice or honeycomb structure. The heating element is then enclosed in the housing.

The great advantage of the active compound chip according to the invention is that differently from all known systems, no external heating apparatus is necessary. The working temperature in each case specific for the determined active compound is generated in the active compound chip using the integrated heating apparatus itself. An over- or underdosage by the user by means of the use of a wrong heating power is excluded. The use is thus simpler, cheaper and safer.

The active compound chip according to the invention advantageously has a high efficiency in the evaporation of the active compound, since the heat is produced by the resistance heater in the interior of the active compound carrier and is utilized for the evaporation of the active compound without losses. The heat energy is thus utilized efficiently. This also means that the heating temperatures for active compounds having low evaporation temperatures can be very low at below 90° C. without losses in the utilization of the active compound in comparison with conventional systems in which a comparable amount of active compound is released only at heating temperatures above 100° C. Using the active compound chip according to the invention, the danger of burning of the user when working with the device is reduced and the evaporation of other constituents of the active compound formulation than the active compound itself can also be reduced to zero. The active compound released is better utilized, since no condensation takes place on the heating apparatus.

The low operating temperature simultaneously makes possible the use of temperature-labile active compounds which can no longer be employed at temperatures of over 100 to 120° C. In exactly the same way, because of the lower working temperature low-melting plastics such as polypropylene and polyethylene can be employed.

As a result of the essentially complete liberation of the active compound, no residue remains in the active compound carrier, which facilitates disposal, in particular if biodegradable polymers are additionally used.

The release of the active compound can take place in a controlled manner since the surface area and the temperature distribution can be defined and controlled accurately, unlike the systems using the heating apparatuses.

The active compound chip according to the invention is flexible in application, since any desired forms can be used and there is no fixing of the space needed by a heating apparatus. If an adapter is to be used, this can be used with different active compounds for various active compound chips having an integrated heating element.

The device according to the invention can be used for the control of insects such as mosquitoes, flies or cockroaches. It can also be used for the evaporation of fragrances or ethereal oils, e.g. in bathrooms or toilets.

BRIEF DESCRIPTION OF THE SEVERAL VIEWS OF THE DRAWINGS

FIG. 3 FIGS. 3a to 3g show the steps of a production process for the production of an active compound chip having an integrated heating element in lattice form and a light diode.

DETAILED DESCRIPTION OF THE INVENTION

Figure 1:
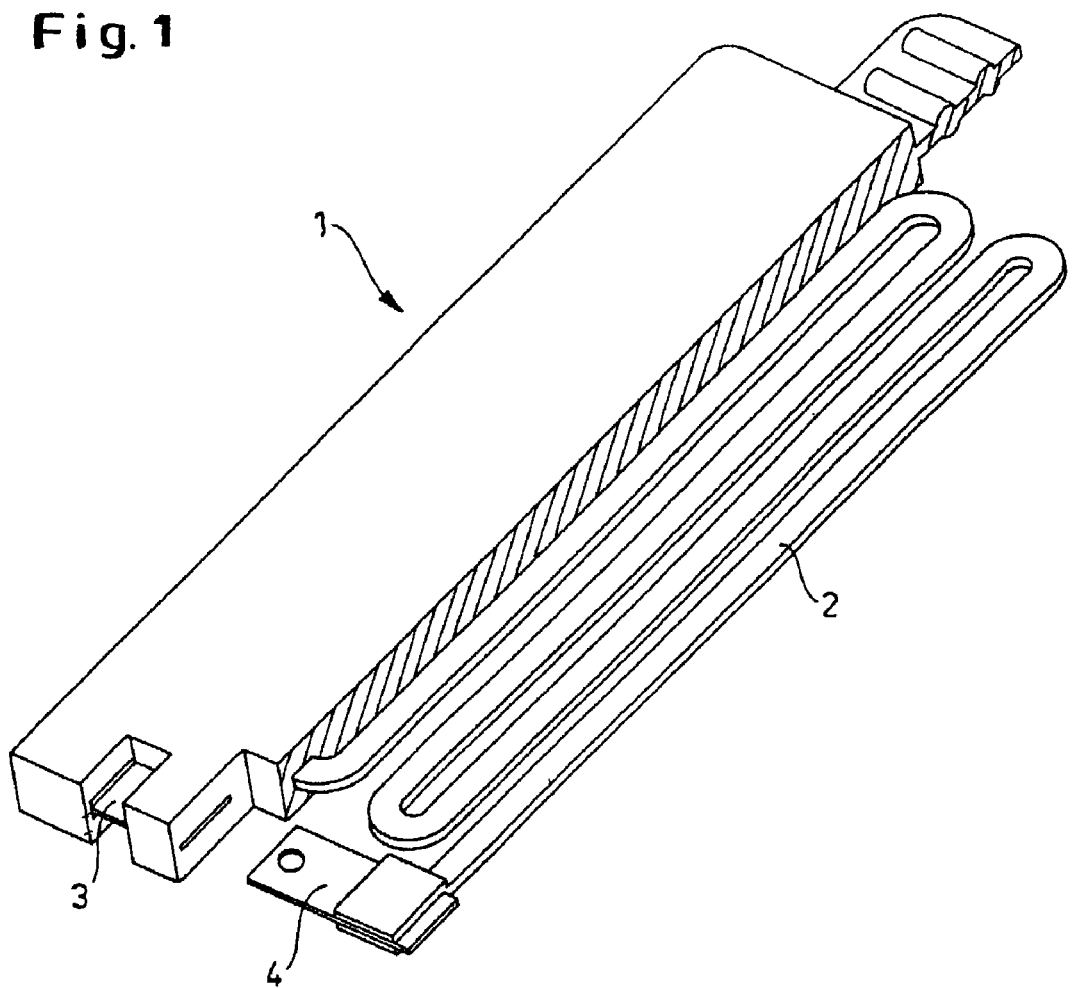
FIG. 1 Perspective view of a plastic plate having an integrated heating element.

FIG. 1 shows a perspective view of an active compound chip 1 having an integrated heating element 2. The heating element 2 has the electrical contacts 3 and 4.

Figure 2A:
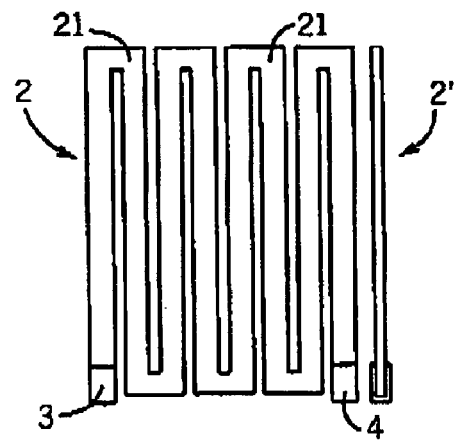
FIG. 2 Schematic representation of possible designs for the heating element.
  a. Meander form having one meander and two contacts.
  b. Meander form having two meanders and two contacts each.
  c. Meander form having two meanders which are connected in an electrically conducting manner.
  d. Meander form having two meanders which are contacted separately.
  e. Lattice form in two strips having an LED.

FIG. 2a shows a heating element 2 in the form of a meander having seven bends 21 and the two contacts 3, 4 in top view and in side view 2.

Figures 2B, 2C, 2D:
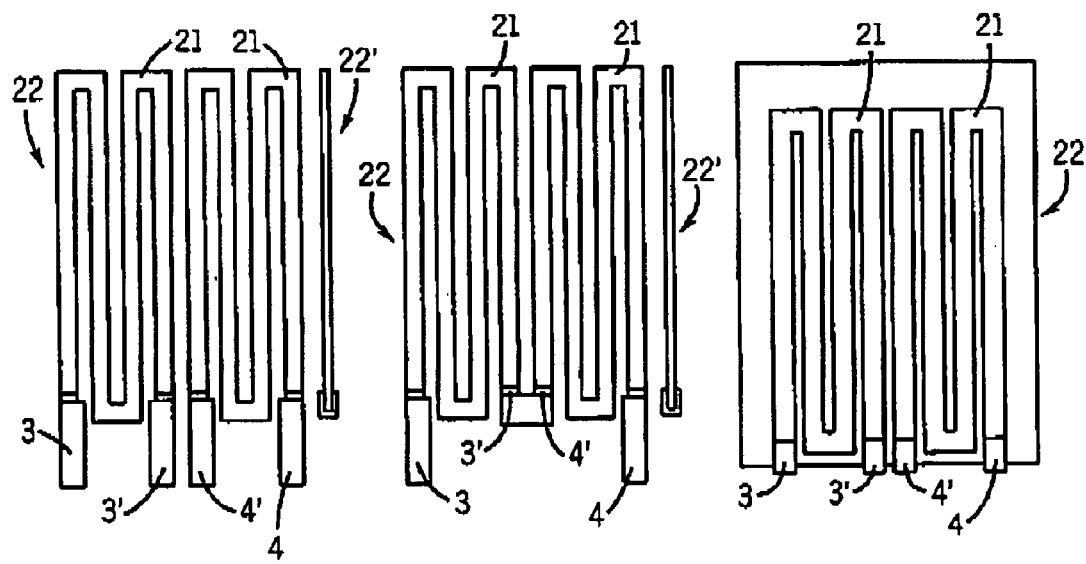

FIG. 2b shows a heating element 22 in the form of two meanders having three bends 21 each and the electrical contacts 3, 3', 4', 4.

FIG. 2c shows a heating element 22 in the form of two meanders having three bends 21 each and the electrical contacts 3, 3', 4', 4 in top view and in side view 22'. The contacts 3' and 4' are connected to one another in an electrically conducting manner. If a voltage of 230 V is applied between the contacts 3 and 4 and the resistance of one meander each is 20 kΩ, according to $P=U^2/R=(230 V)^2/(20 k\Omega+20 k\Omega)$ approximately P=1.32 W of heating power results.

FIG. 2d shows a heating element 22 in the form of two meanders having three bends 21 each and the electrical contacts 3, 3', 4', 4 in top view and in side view 22'. If a voltage of 110 V is applied between each of the contacts 3 and 3' and 4' and 4 and the resistance of each meander is 20 kΩ, according to $P=U^2/R=(110 V)^2/(20 k\Omega)+(110 V)^2/(20 k\Omega)$ approximately P=1.32 W of heating power results.

Figure 2E:
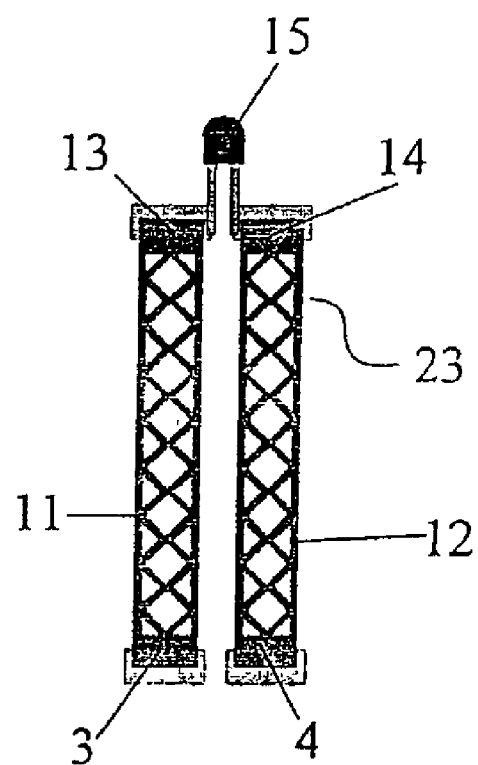

FIG. 2e shows a heating element 23 in the form of a lattice having two strips 11, 12 The contacts 3, 4 are located at the two corresponding ends of the strips 11, 12. The opposite ends 13 and 14 are connected in an electrically conducting manner via a light diode 15.

The steps of a production process for the production of an active compound chip having an integrated heating element and light diode according to FIG. 2e are shown in FIGS. 3a to 3g.

Figure 3A:
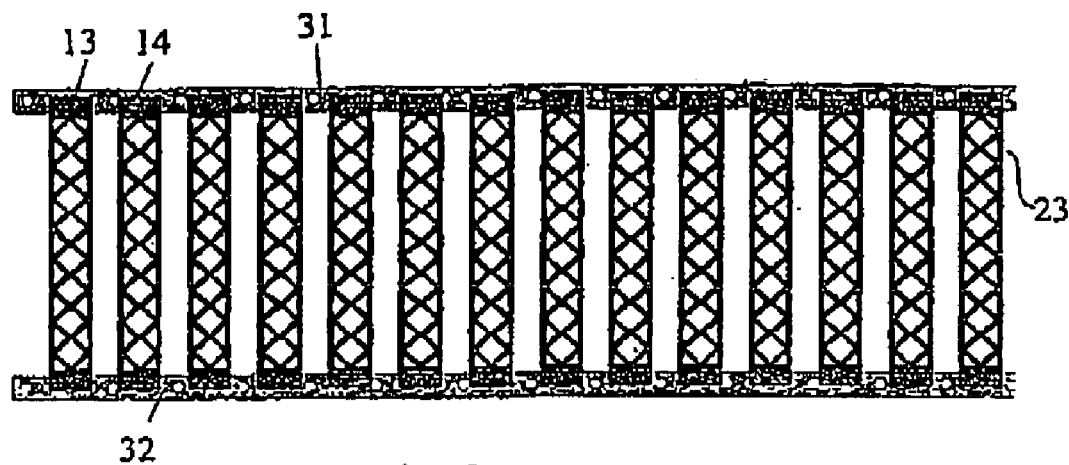
Figure 3B:
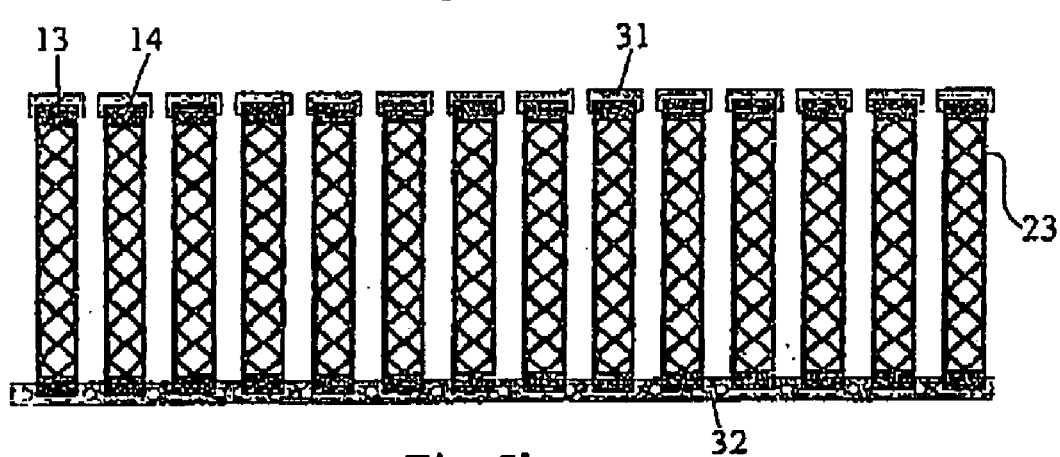
Figure 3C:
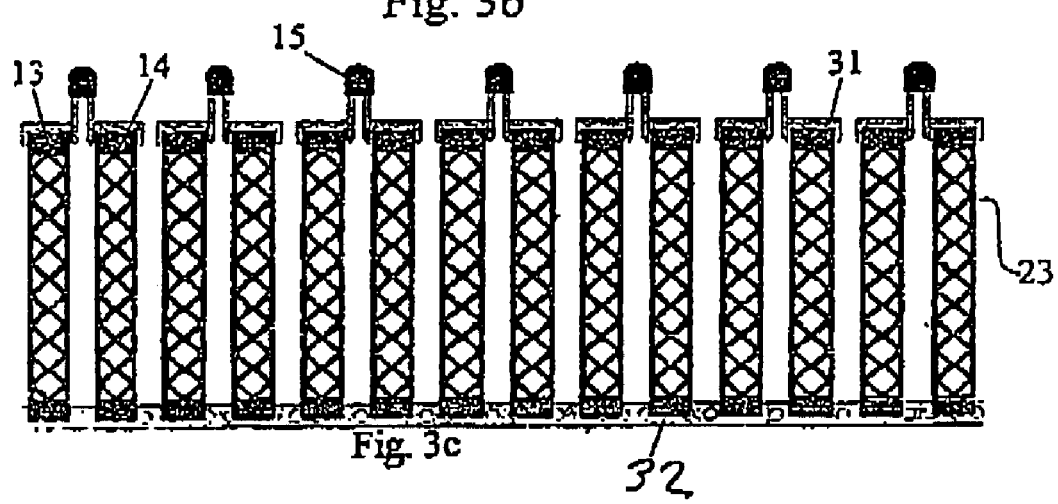
Figure 3D:
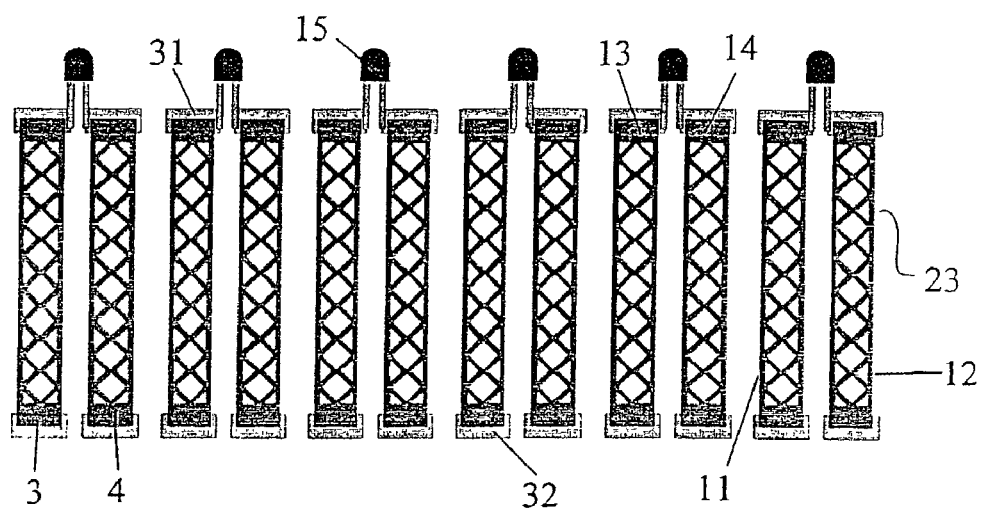
Figure 3E:
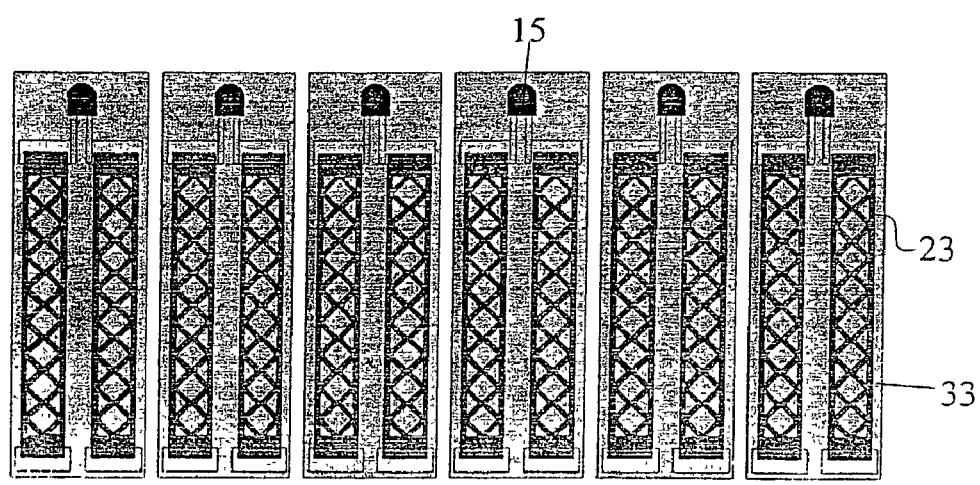
Figure 3F:
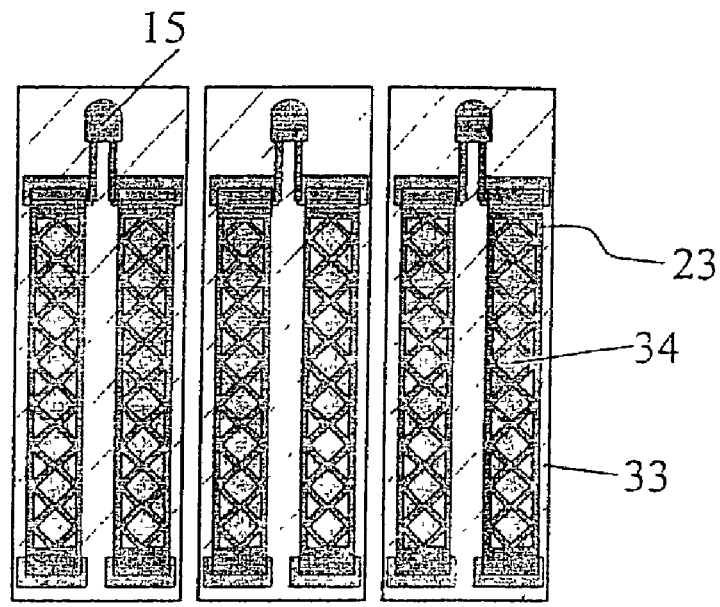
Figure 3G:
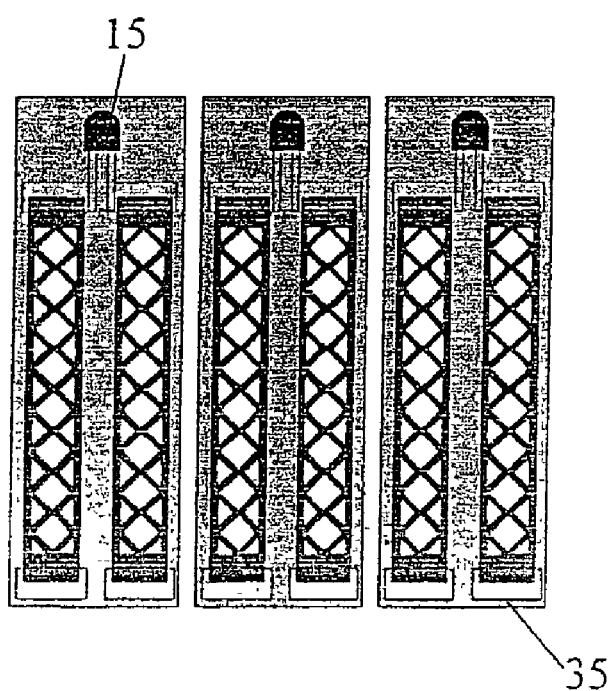

Two perforated brass tapes 31, 32 run through a spraying machine and strip-shaped heating elements 23 of conductive plastic in the form of a lattice are sprayed onto the brass tapes with their ends 13, 14 (FIG. 3a). The brass tape 31 is cut between the ends 13, 14 (FIG. 3b). An LED 15 is soldered between the two free ends 13, 14 (FIG. 3c). The brass tape 32 is then separated between the contacts 3, 4 and separate heating elements 23 are obtained (FIG. 3d). Following this, each heating element 23 is enclosed in a housing subsection 33 (FIG. 3e) and the active compound 34 is introduced into the housing (FIG. 3f). Finally, the housing upper section 35 is mounted (FIG. 3g).

EXAMPLES

Example 1

Assembly and Application an Active Compound Chip Having an Integrated Heating Apparatus A heating element 2 having a cross section of 1 mm and a length of 67 mm and an electrical resistance of about 15 Ω was cast into a plastic plate according to FIG. 1 made of polypropylene material and of 70 mm length, 30 mm breadth and 5 mm thickness. The heating element had the form of a meander. The plastic material of which the plastic plate consisted contained between 8.1% and 8.4%, altogether about 720 mg, of the active compound transfluthrin.

The plastic plate was attached to the socket (230 V) via the electrical contacts 3 and 4 by means of an adapter with a mains receiver. The voltage at the electrical resistance of the active compound chip was 230 V. Within a few minutes, the wire in the plastic plate heated up to 65 to 70° C. and the active compound transfluthrin began to evaporate in a biologically active amount. The working temperature was kept in the range from 65 to 90° C. over a period of time of 8 hours. After 45 of these 8 hour cycles, it was still possible to detect a proportion of about 70% of the original amount of active compound in the active compound chip. A pause of 16 hours was made between two successive cycles. The room temperature during the experiment was 21 to 25° C.

Example 2

Comparison of the Working Temperatures of Various Vaporator Systems

The properties of an active compound chip having an integrated heating element according to example 1 has been compared with the properties of three other evaporator systems, which are also long-term systems, i.e. have a reservoir of active compound for a number of days.

The first comparison system chosen was a gel evaporator. 1.6 g of the formulation of the gel evaporator had the following composition:

| | |
|---|---|
| 37.5% of pure Transfluthrin ® = | 600.0 mg |
| 4.5% of Aerosil 200 ® = | 72.0 mg |
| 0.03% of Sudan Blue 670 ® dye = | 0.48 mg |
| 2.0% of Baygona 226863 ® perfume oil = | 32.0 mg |
| 55.97% of Diphyl THT ® = | 895.52 mg |
| = | 1600.00 mg |

The evaporation was carried out by means of an appropriate heating apparatus at a temperature of 100 to 110° C.

The second comparison system chosen was a liquid evaporator. 35 g of the formulation of the liquid evaporator had the following composition:

| | |
|---|---|
| 0.88% of transfluthrin; = | 0.308 g |
| 67.12% of Isopar M; = | 23.492 g |
| 30.0% of Isopar V = | 10.5 g |
| 1.0% of butylhydroxy toluene = | 0.35 g |
| 1.0% of Deodorins B.Y.R. N 3 perfume oil = | 0.35 g |
| = | 35.0 g |

The evaporation was carried out by means of an appropriate heating apparatus at a temperature of 125 to 135° C.

The third comparison system chosen was a polymeric active compound carrier having an external heating apparatus. The same plastic material and the same amount of active compound as in example 1 was used.

The evaporation was carried out by means of an appropriate heating apparatus at temperatures of 100° C. and 150° C.

All experiments were carried out at a room temperature of 21 to 25° C.

Table 1 shows the working temperatures measured for the various evaporator systems. The working temperature is that temperature at which an adequate biological action occurs. The comparison presented in Table 1 shows that the working temperature of the active compound chip having an integrated heating element at 65 to 90° C. is markedly below the working temperature of the known evaporator systems. The polymeric active compound carrier, which has the same composition as the active compound chip according to the invention as in example 1 and only, differently to the active compound chip according to the invention, has no integrated heating apparatus, but an external heating apparatus, showed a working temperature in the range from 140° C. to 150° C. At temperatures in the range from 110° C. and 100° C., the biological action noticeably decreased. The plate evaporator was used in its commercially obtainable form (PV 3 heater, DBK).

TABLE 1

Working temperature of various evaporator systems in comparison

| System | Temperature range |
|---|---|
| Plate evaporator | 140–150° C. |
| Liquid evaporator | 125–135° C. |
| Gel evaporator | 100–110° C. |

TABLE 1-continued

Working temperature of various evaporator systems in comparison

| System | Temperature range |
|---|---|
| Active compound chip | 65–90° C. |
| Polymeric active compound carrier | 140–150° C. |

Example 3

Comparison of the Evaporation Rates of Various Evaporator Systems

A long-term test of the evaporation rate of active compound was carried out in comparison of the active compound chip with the gel evaporator and the liquid evaporator.

The cycle duration was 8 hours with 16 hours interruption between two successive cycles.

The working temperature of the systems was chosen as in Table 1 such that it was possible to achieve a comparable biological action.

The results of the comparison of the evaporation rates over 45 cycles are shown in Tables 2 to 5. Table 2 shows the release rates of the total formulations and Table 3 the average values of these release rates. Table 4 indicates how much active compound was released in the individual cycles and Table 5 the average value of the release rates of the active compound.

Figure 4:
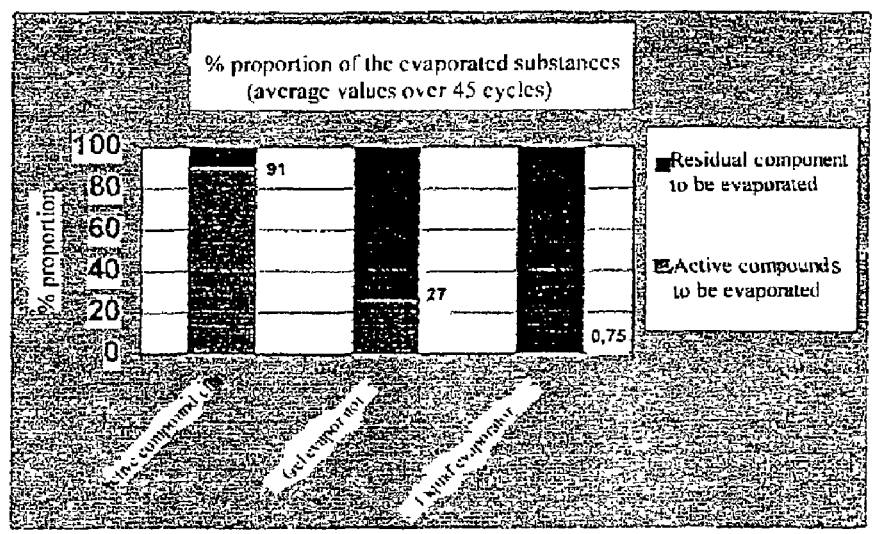
FIG. 4 Average values of proportions of the evaporated substances over 45 cycles.

The weight loss of the total formulation of the individual systems is composed of evaporated active compound and evaporation of additional constituents of the formulation. The amount of the total formulation evaporated in the gel evaporator and in the liquid evaporator is markedly higher than in the active compound chip (Table 2). A comparison of the amount of evaporated active compound shows that the amount of active compound evaporated in the active compound chip, the amount of active compound evaporated in the gel evaporator and in the liquid evaporator corresponds down to 1 to 2 mg/cycle (Table 4). This confirms that the chosen working temperatures lead to comparable biological actions due to a comparable amount of evaporated active compound. If, however, the proportion of active compound of the total amount evaporated is considered, it is seen that that this amount in the active compound chip is 100% from the 4th cycle, between 25% and 35% for the gel evaporator and below 1% for the liquid evaporator. It emerges from Table 6 how much active compound was evaporated in relation to the overall amount evaporated. This was on average 91% over all 45 cycles in the active compound chip, 27% in the gel evaporator and 0.75% in the liquid evaporator. In the starting cycles (1st to 7th cycle), the proportion of active compound in all three systems is lower than in the last cycles (40th to 45th cycle). FIG. 4 illustrates how the total amount of substance evaporated is composed of proportions of active compound and other proportions for the three systems tested.

The good ratio of active compound to the total amount evaporated in the active compound chip is to be attributed to the formulation associated with the low working temperature which is possible due to the integrated heating apparatus. The evaporation temperature for the polypropylene material in which the active compound is embedded is markedly above 100° C., while for the evaporation of an adequate amount of active compound a working temperature of below 100° C. suffices. In all comparison systems, the temperature which is necessary for the evaporation of an adequate amount of active compound is also over 100° C., so that large proportions of the other material are automatically evaporated with the active compound.

The almost 100% proportion of active compound in the total amount evaporated in the active compound chip has the advantage of lower pollution of the environment with comparable biological activity in relation to the known evaporator systems. The lower pollution of the environment with the active compound chip in comparison is also manifested by the uniform, low evaporation rate.

The evaporation rate over the total experimental period for the active compound chip has an absolute variation width which is markedly below the variation width for the gel evaporator and the liquid evaporator (Table 3). The absolute variation width of the evaporation rate of active compound over the total experimental period is comparable in all three cases investigated and is between 0.6 mg/cycle (liquid evaporator) and 0.9 mg/cycle (gel evaporator) (Table 4).

TABLE 2

Release rate of the total formulation

| Cycle | Active compound chip Weight loss [mg/cycle] | Gel evaporator Weight loss [mg/cycle] | Liquid evaporator Weight loss [mg/cycle] |
|---|---|---|---|
| 1 | 17.6 | 37 | 1010 |
| 2 | 11.2 | 38 | 890 |
| 3 | 11.3 | 33 | 887 |
| 4 | 7.5 | 33 | 885 |
| 5 | 6.8 | 26 | 880 |
| 6 | 5.4 | 26 | 870 |
| 7 | 2.8 | 26 | 860 |
| 8 | 6.7 | 26 | 850 |
| 9 | 4.3 | 26 | 850 |
| 10 | 5.7 | 26 | 840 |
| 11 | 5.7 | 26 | 840 |
| 12 | 5.3 | 22 | 840 |
| 13 | 4.8 | 22 | 830 |
| 14 | 6.2 | 22 | 820 |
| 15 | 5.0 | 22 | 820 |
| 16 | 3.6 | 22 | 820 |
| 17 | 2.6 | 22 | 820 |
| 18 | 3.0 | 19 | 820 |
| 19 | 4.3 | 19 | 820 |
| 20 | 4.1 | 18 | 800 |
| 21 | 3.8 | 18 | 800 |
| 22 | 4.2 | 16 | 800 |
| 23 | 3.5 | 16 | 790 |
| 24 | 3.2 | 16 | 790 |
| 25 | 3.2 | 16 | 790 |
| 26 | 3.1 | 16 | 780 |
| 27 | 3.0 | 16 | 770 |
| 28 | 3.5 | 17 | 770 |
| 29 | 4.5 | 17 | 770 |
| 30 | 4.3 | 11 | 770 |
| 31 | 3.6 | 11 | 770 |
| 32 | 3.4 | 10 | 770 |
| 33 | 2.4 | 10 | 770 |
| 34 | 3.4 | 10 | 770 |
| 35 | 4.3 | 10 | 780 |
| 36 | 1.9 | 10 | 760 |
| 37 | 1.8 | 10 | 760 |
| 38 | 1.8 | 10 | 760 |
| 39 | 2.5 | 10 | 770 |
| 40 | 2.7 | 9 | 775 |
| 41 | 2.8 | 9 | 760 |
| 42 | 3.0 | 7 | 760 |
| 45 | 3.0 | 6 | 680 |

TABLE 3

Average values of the release rate of the total formulation

| System | Average value [mg]/cycle | Standard deviation +/− [mg]/cycle |
|---|---|---|
| Active compound chip | 4.6 | 1.45 |
| Gel evaporator | 18.4 | 4.1 |
| Liquid evaporator | 809 | 28 |

TABLE 4

Release rate of the active compound

| Cycle | Active compound chip Weight loss [mg/cycle] | Gel evaporator Weight loss [mg/cycle] | Liquid evaporator Weight loss [mg/cycle] |
|---|---|---|---|
| 1 | 7.1 | 9.3 | 6.8 |
| 2 | 7.2 | 9.5 | 7 |
| 3 | 7.3 | 7.6 | 7.5 |
| 4 | 7.5 | 7.6 | 6.5 |
| 5 | 6.8 | 6.8 | 7.9 |
| 6 | 5.4 | 6.6 | 7.2 |
| 7 | 2.8 | 6.7 | 5.5 |
| 8 | 6.7 | 6.7 | 7.6 |
| 9 | 4.3 | 6.8 | 6.5 |
| 10 | 5.7 | 6.9 | 7.6 |
| 11 | 5.7 | 7.1 | 7.5 |
| 12 | 5.3 | 5.9 | 5.3 |
| 13 | 4.8 | 5.5 | 7.4 |
| 14 | 6.2 | 5.7 | 4.8 |
| 15 | 5 | 5.8 | 6.5 |
| 16 | 3.6 | 5.9 | 6.4 |
| 17 | 2.6 | 6 | 6.3 |
| 18 | 3 | 4.7 | 7.1 |
| 19 | 4.3 | 4.5 | 6.5 |
| 20 | 4.1 | 4.4 | 7.2 |
| 21 | 3.8 | 4.3 | 7 |
| 22 | 4.2 | 4.1 | 7 |
| 23 | 3.5 | 4.2 | 7.1 |
| 24 | 3.2 | 4.3 | 7.1 |
| 25 | 3.2 | 4.4 | 7 |
| 26 | 3.1 | 4.1 | 7.1 |
| 27 | 3 | 4.2 | 6.9 |
| 28 | 3.5 | 4.4 | 6.2 |
| 29 | 4.5 | 4.3 | 6.1 |
| 30 | 4.3 | 3.9 | 5.8 |
| 31 | 3.6 | 3.8 | 5.6 |
| 32 | 3.4 | 3.3 | 5.2 |
| 33 | 2.4 | 3.2 | 5.1 |
| 34 | 3.4 | 3.2 | 5 |
| 35 | 4.3 | 3.1 | 4.5 |
| 36 | 1.9 | 3 | 4.4 |
| 37 | 1.8 | 3.3 | 4.3 |
| 38 | 1.8 | 3.1 | 4.2 |
| 39 | 2.5 | 3 | 4.1 |
| 40 | 2.7 | 2.7 | 4 |
| 41 | 2.8 | 2.5 | 3.9 |
| 42 | 3 | 2.4 | 3.8 |
| 45 | 3 | 2.3 | 3.8 |

TABLE 5

Average values of the release rate of the active compound

| | Average value [mg]/cycle | Standard deviation +/− [mg]/cycle |
|---|---|---|
| Active compound chip | 4.2 | 0.8 |
| Gel evaporator | 4.9 | 0.9 |
| Liquid evaporator | 6.1 | 0.6 |

TABLE 6

Proportion of the active compound in the total amount of the substances evaporated (average value over 45 cycles) in [%]

|  | Ø over 45 cycles | Starting cycles (1–7) | End cycles (40–45) |
|---|---|---|---|
| Active compound chip | 91 | 86 | 100 |
| Gel evaporator | 27 | 25 | 70 |
| Liquid evaporator | 0.75 | 0.5 | 3.0 |

Example 4

Comparison of the Amounts of Active Compound of Various Evaporator Systems Necessary for a Comparable Biological Action An advantage of the active compound chip is seen in that an identical amount of active compound evaporated as in the gel evaporator and in the liquid evaporator has a better biological action. This lies in the fact that in the gel evaporator and in the liquid evaporator a part of the active compound evaporated is directly lost again by condensation on cool sites of the heating apparatus, while the active compound evaporated in the active compound chip is almost completely utilized. Table 7 indicates how much active compound must in each case be evaporated using the active compound chip, the gel evaporator and the liquid evaporator in order that a comparable biological action occurs. A reduction in the needed amount of active compound evaporated has a positive effect on the reduction of the environmental pollution, the longevity and the temperature.

TABLE 7

Amount of active compound which produces the same biological action

| Active compound chip | Gel evaporator | Liquid evaporator |
|---|---|---|
| Amount per cycle [mg/8 h] | | |
| 4.2 | 4.9 | 6.1 |
| Amount per hour (index) [mg/h] | | |
| 0.5 (100) | 0.6 (120) | 0.8 (160) |

Example 5

The Biological Action of the Active Compound Chips

The biological action of active compound chips having an integrated heating element on the mosquitoes of the species Aedes Aegypti, sensitive was demonstrated in example 5.

The experiment was carried out in a room of 36 m³ size, having an open window, at a temperature of 20 to 28° C. and rel. room humidity of 17 to 34%. The working temperature was 65 to 90° C. Active compound chips according to example 1 were

TABLE 8

Biological action of the active compound chip

| Operating time/testing after days | Mosquito estimate after | Formulation Example 1 Knockdown action after min or % dead after h | | | |
|---|---|---|---|---|---|
| (Hours) | hours | 50% | 100% | 9 h | 24 h |
| 1st day | 0 | 46' | 55' | 100 | 100 |
|  | 1 | 16' | 32' | 100 | 100 |
|  | 2 | 9' | 28' | 100 | 100 |
|  | 3 | 11' | 23' | 100 | 100 |
|  | 4 | 13' | 19' | 100 | 100 |
|  | 5 | 12' | 23' | 100 | 100 |
| 8 hours | 6 | 23' | 43' | 100 | 100 |
|  | 7 | 33' | 1 h 00' | 100 | 100 |
|  | 8 | 26' | >8 h | 88 | 100 |
| 2 days | 0 | 44' | 1 h 14' | 100 | 100 |
|  | 1 | 59' | 1 h 19' | 100 | 100 |
|  | 2 | 36' | 1 h 03' | 100 | 100 |
|  | 3 | 19' | 49' | 100 | 100 |
|  | 4 | 19' | 53' | 100 | 100 |
|  | 5 | 46' | 1 h 12' | 100 | 100 |
|  | 6 | 29' | 1 h 17' | 100 | 100 |
|  | 7 | 24' | 43' | 100 | 100 |
| 16 hours | 8 | 14' | 32' | 100 | 100 |
| 3 days | 0 | 40' | 48' | 100 | 100 |
|  | 1 | 9' | 13' | 100 | 100 |
|  | 2 | 3' | 5' | 100 | 100 |
|  | 3 | 3' | 6' | 100 | 100 |
|  | 4 | 2' | 4' | 100 | 100 |
|  | 5 | 3' | 7' | 100 | 100 |
|  | 6 | 5' | 11' | 100 | 100 |
|  | 7 | 7' | 16' | 100 | 100 |
| 24 hours | 8 | 4' | >1 h | 90 | 100 |

The results show the expected biological action of the system. The application time can be adjusted by variation of the active compound concentration in the active compound chip.

The invention claimed is:

1. An active compound chip comprising an active compound which is bound at room temperature to an active compound carrier, characterized in that at least one heating element of the chip has an electrical resistance portion and two electrical contacts, wherein the electrical resistance portion is integrated at least partly in the interior of the chip and at least partially embedded in, in the form of being cast in, the active compound carrier to produce heat from within the chip, wherein the chip is not equipped with a heating apparatus that provides heat to the chip externally, and wherein the active compound carrier is in contact with the electrical resistance portion.

2. The active compound chip as claimed in claim 1, characterized in that the heating element can be heated and the active compound can be evaporated by applying an electrical voltage to the electrical contacts.

3. The active compound chip as claimed in claim 1, characterized in that it forms a rectangular plate and has a length in the range from 10 to 100 mm, a breadth in the range from 5 to 100 mm and a thickness in the range from 3 to 20 mm.

4. The active compound chip as claimed in claim 1, characterized in that the heating element consists of a conductive material which can be processed mechanically.

5. The active compound chip as claimed in claim 4, characterized in that the heating element consists of ceramic, heat conductor, vapor-deposited film or conductive plastic.

6. The active compound chip as claimed in claim 1, characterized in that the heating element consists of a heating resistance or PTC.

7. The active compound chip as claimed in claim 1, characterized in that the heating element has a resistance of 10 kΩ to 100 KΩ.

8. The active compound chip as claimed in claim 1, characterized in that the heating element has a resistance of 2 kΩ to 30 KΩ.

9. The active compound chip as claimed in claim 1, characterized in that the heating power of the heating element is between 0.1 W and 5 W.

10. The active compound chip as claimed in claim 1, characterized in that a temperature in the range from 60° C. to 140° C. can be established using the heating element.

11. The active compound chip as claimed in claim 1, characterized in that the heating element is arranged in the form of a meander having at least one bend, the two electrical contacts being located on the two ends of the meander.

12. The active compound chip as claimed in claim 1, characterized in that the electrical contacts consist of sheet brass or copper.

13. The active compound chip as claimed in claim 1, characterized in that the active compound used is selected from the group consisting of pyrethroids, acaricidal active compounds, fragrances and ethereal oils.

14. The active compound chip as claimed in claim 13, characterized in that the active compound used is Transfluthrin® or Pynamin forte® or benzyl benzoate.

15. The active compound chip as claimed in claim 1, characterized in that the active compound can be evaporated at a temperature below 100° C.

16. The active compound chip as claimed in claim 15, wherein the active compound can be evaporated at a temperature in the range of 65° C. to 90° C.

17. The active compound chip as claimed in claim 1, characterized in that, after a starting phase of 5 8-hour cycles, the amount of total formulation evaporated on average over a cycle contains at least 70% of active compound.

18. The active compound chip as claimed in claim 17, wherein the amount of total formulation evaporated on average over a cycle contains at least 90% of active compound.

19. The active compound chip as claimed in claim 18, wherein the amount of total formulation evaporated on average over a cycle contains more than 99% of active compound.

20. An active compound chip comprising an active compound which is bound at room temperature to an active compound carrier, characterized in that at least one heating element of the chip has an electrical resistance portion and two electrical contacts, wherein the electrical resistance portion is integrated at least partly in the interior of the chip and at least partially embedded in, in the form of being cast in, the active compound carrier to produce heat from within the chip, wherein the chip is not equipped with a heating apparatus that provides heat to the chip externally and wherein the heating element is surrounded, according to its length, by the chip part comprising the active compound carrier so that the shape of the heating element forms an image on the external shape of the active compound chip, and wherein the active compound carrier is in contact with the electrical resistance portion.

21. The active compound chip as claimed in claim 20, characterized in that the active compound carrier is a polymer.

22. The active compound chip as claimed in claim 21, characterized in that the active compound carrier consists of plastic material and the active compound consists of Transfluthrin®.

23. The active compound chip as claimed in claim 22 wherein the plastic material is selected from the group consisting of polyethylene, polypropylene, TPX® type plastic, Desmopan® 8410, Vestamid® 1800, and BAK® 402-005.

24. The active compound chip as claimed in claim 20, characterized in that the chip consists essentially of the heating element and the active compound carrier containing active compound surrounding this.

* * * * *